United States Patent [19]

Toogood

[11] Patent Number: 4,624,849

[45] Date of Patent: Nov. 25, 1986

[54] ANTIMICROBIAL LOZENGES

[75] Inventor: Kevin C. Toogood, Cincinnati, Ohio

[73] Assignee: The Procter & Gamble Company, Cincinnati, Ohio

[21] Appl. No.: 667,678

[22] Filed: Nov. 2, 1984

[51] Int. Cl.$^4$ .......................... A61K 7/22; A61K 9/20; A61K 31/74

[52] U.S. Cl. .......................... 424/78; 424/48; 424/49; 424/54; 514/960

[58] Field of Search .......................... 424/48-58, 424/78; 514/960

[56] References Cited

U.S. PATENT DOCUMENTS

| | | | |
|---|---|---|---|
| 2,540,253 | 2/1951 | Gakenheimer | 424/78 |
| 3,096,248 | 7/1963 | Rudzki | 424/33 |
| 3,200,039 | 8/1965 | Thompson | 424/14 |
| 3,271,256 | 9/1966 | Frey | 514/758 |
| 3,431,339 | 3/1969 | Gyarmathy et al. | 424/52 |
| 3,432,592 | 3/1969 | Speiser | 424/19 |
| 3,439,089 | 4/1969 | Cherkas et al. | 424/78 |
| 3,511,914 | 5/1970 | Wolkoff et al. | 514/772 |
| 3,594,467 | 7/1971 | Christenson et al. | 424/19 |
| 4,098,879 | 7/1978 | Cousse et al. | 424/52 |
| 4,169,885 | 10/1979 | Raaf et al. | 424/16 |
| 4,256,731 | 3/1981 | Curtis et al. | 424/54 |
| 4,327,076 | 4/1982 | Puglia et al. | 424/38 |

FOREIGN PATENT DOCUMENTS 026252  4/1981  European Pat. Off. .

OTHER PUBLICATIONS

Stokely-VanCamp, Inc. Data Sheet on Sterotex.
Serponelloni C. A. 101#169425g (1984) of FR. 2537844, 22 Jun. 1984.
Bhargava et al. C. A. 98#221757c (1983).
Ban et al. CA. 97#11773H (1982).
Pinzauti et al. CA. 92#47191C (1980).
Kristofferrson et al. CA. 89#135786u (1978).
Frosch et al. CA. 89#191672r (1978).
Gobba et al. CA. 74#73221k (1971).

*Primary Examiner*—Shep K. Rose
*Attorney, Agent, or Firm*—Richard C. Witte; John V. Gorman; Douglas C. Mohl

[57] ABSTRACT

Lozenges are disclosed which contain a cationic therapeutic agent effective against plaque and gingivitis and a nonionic lubricant.

8 Claims, No Drawings

ANTIMICROBIAL LOZENGES

TECHNICAL FIELD

The present invention relates to therapeutic lozenges which contain a cationic antimicrobial effective against plaque and gingivitis and a nonionic lubricant. The lozenges of the present invention provide a convenient and effective way to apply the antimicrobial agent in the mouth.

BACKGROUND ART

The use of cationic antimicrobial agents to reduce plaque and gingivitis has been recognized for many years. Included among references disclosing, such compositions are U.S. Pat. No. 3,937,805, Feb. 10, 1976 to Harrison; U.S. Pat. No. 3,937,807, Feb. 10, 1976 to Haefele; U.S. Pat. No. 4,080,441, Mar. 21, 1978 to Gaffar et al.; U.S. Pat. No. 4,118,474, Oct. 3, 1978 to Gaffar et al.; U.S. Pat. No. 4,241,049, Dec. 23, 1980 to Colodney et al.; U.S. Pat. No. 3,925,543, Dec. 9, 1975 to Donohue; U.S. Pat. No. 4,256,731, Mar. 17, 1981 to Curtis et al.; U.S. Pat. No. 4,217,342, Aug. 12, 1980 to Gaffar; U.S. Pat. No. 4,259,316, Mar. 31, 1981 to Nakashima et al.; U.S. Pat. No. 4,309,409, Jan. 4, 1982 to Coll-Palagos et al.; and U.S. Pat. No. 4,169,885, Oct. 2, 1979 to Raaf et al. In addition lozenges containing cationic antimicrobials have been sold and the patents to Curtis et al. and Raaf et al. disclose lozenges but not of the type of the present invention.

Plaque is a term commonly used to describe the colonization and growth of microorganisms on both the surface and subsurface regions of the teeth. Antimicrobials have been shown to be able to interrupt this cycle and thereby reduce the level of plaque formed but have oftentimes caused unacceptable levels of staining. Maintaining a high level of efficacy and acceptable staining has proven to be difficult to achieve.

It has now been found with the present lozenges that concentration of the antimicrobial in the mouth as the lozenge dissolves can be minimized without compromising the level of active in saliva after dissolution of the lozenge, which is therapeutically effective against plaque and gingivitis.

It is therefore an object of the present invention to formulate effective antiplaque/antigingivitis compositions. By reducing plaque, caries may also be reduced.

It is a further object of the present invention to formulate antiplaque/antigingivitis compositions which have reduced staining.

These and other objects will become more apparent from the detailed description which follows. All percentages and ratios herein are by weight unless otherwise specified.

SUMMARY OF THE INVENTION

The present invention relates to therapeutic lozenges containing a safe and effective amount of a cationic antimicrobial agent and a nonionic lubricant. The lozenges in addition contain pharmaceutically acceptable lozenge materials which are not cariogenic and are compatible with the cationic antimicrobial agent. The necessary as well as optional ingredients are described in detail below.

DETAILED DESCRIPTION OF THE INVENTION

The ingredients used in the present compositions are described below as well as certain terms.

By "safe and effective amount of cationic antimicrobial", as used herein, means a sufficient amount to reduce plaque while being safe to the hard and soft tissues of the oral cavity.

By "compatible with the cationic antimicrobial", as used herein, is meant that any material present in the lozenge will not form an insoluble precipitate with the cationic antimicrobial.

By the term "cariogenic", as used herein, is meant substances capable of increasing the natural caries rate in the mouth.

By the term "comprising", as used herein, is meant that various additional components can be conjointly employed in the compositions of this invention as long as the cationic antimicrobial can perform its intended function.

CATIONIC ANTIMICROBIAL

The antimicrobials used in the compositions of the present invention can be any of a wide variety of cationic antimicrobial agents such as quaternary ammonium compounds (e.g. cetyl pyridinium chloride), and substituted guanidines such as chlorhexidine and the corresponding compound alexidine. Mixtures of cationic antimicrobials may also be used in the present invention.

Antimicrobial quaternary ammonium compounds include those in which one or two of the substituents on the quaternary nitrogen has a carbon chain length (typically alkyl group) of some 8 to 20, typically 10 to 18 carbon atoms while the remaining substituents (typically alkyl or benzyl group) have a lower number of carbon atoms, such as 1 to 7 carbon atoms, typically methyl or ethyl groups. Dodecyl trimethyl ammonium bromide, tetradecyl pyridinium chloride, tetradecyl ethyl pyridinium chloride, dodecyl dimethyl(2-phenoxyethyl)ammonium bromide, benzyl dimethylstearyl ammonium chloride, cetyl pyridinium chloride, quaternized 5-amino-1,3-bis(2-ethyl-hexyl)-5-methyl hexa hydropyrimidine and benzethonium chloride are exemplary of typical quaternary ammonium antibacterial agents. Other compounds are the bis[4-(R-amino)-1-pyridinium]alkanes as disclosed in U.S. Pat. No. 4,206,215, June 3, 1980 to Bailey incorporated herein by reference. The pyridinium compounds are the preferred quaternary ammonium compounds.

The substituted guanidines of this invention include bisbiguanide compounds having the generic formula

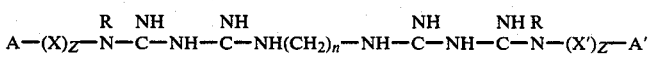

wherein A and A' each represent either (1) a phenyl radical which optionally is substituted by an alkyl or alkoxy group containing from 1 to about 4 carbon atoms, a nitro group, or a halogen atom; (2) an alkyl group containing from about 1 to about 12 carbon atoms; or (3) alicyclic groups containing from 4 to about 12 carbon atoms; wherein X and X' each represent an alkylene radical containing from 1 to 3 carbon atoms;

wherein Z and Z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; wherein the polymethylene chain $(CH_2)_n$ may optionally be interrupted by oxygen or sulfur atoms, aromatic nuclei, etc. The water soluble salts of the above compounds are preferred for use herein. Suitable water soluble salts include the chloride, the fluoride, and especially the acetate salt. The preferred substituted guanidine is chlorhexidine-[1,6-di(-$N^5$-pchlorophenyl-N-diguanido)-hexane].

The cationic antimicrobial is generally used in the present compositions at a level of from about 0.02% to about 1%, preferably from about 0.3% to about 0.7% most preferably from about 0.3% to about 0.5%.

NONIONIC LUBRICANTS

The use of a lubricant in the manufacture of compressed lozenges is to facilitate the release of the lozenge from the die in which it is formed. This function is described in detail in *Pharmaceutical Dosage Forms: Tablets, Volume* 1 edited by H. A. Lieberman and L. Lochman, New York; Marcel Dekker, Inc., 1980 incorporated herein by reference.

The lubricant used in the present invention is a solid material which is not charged and which will not interfere (e.g. complex) with the cationic antimicrobial. The material should preferably be water insoluble. One type of suitable material meeting these requirements is a non-toxic hydrocarbon fat or derivative. Examples include hydrogenated tallow and hydrogenated vegetable oil. Polyethylene glycols may also be used as a lubricant so long as they are solid materials which generally means having a molecular weight in the 4000 to 6000 range. These materials can also be used as a filler as noted below.

Mixtures of lubricants may also be used in the present invention. The lubricant is used at a level of from about 0.1% to about 4.0% preferably from about 0.5% to about 2%.

LOZENGE VEHICLE

The "vehicle" as the term is used herein is the material(s) which carries the cationic antimicrobial and the nonionic lubricant. These materials are also known as "fillers". Since the vehicle is non-cariogenic the vehicle should be free of sucrose and similar materials. Acceptable filler materials include mannitol, sorbitol, xylitol, polyethylene glycol and non-cariogenic dextrans. The fillers may be used alone or in combination.

Mannitol is a naturally occurring sugar alcohol and is available as a fine powder. It has a sweetness of only about 50% of that of sucrose. However, mannitol's negative heat of solution enables it to impart a pleasant, cooling sensation in the mouth as the lozenge dissolves.

Sorbitol is a chemical isomer of mannitol and possesses a similar degree of sweetness. Its heat of solution, being negative, also provides for a pleasant, cooling sensation in the mouth. Sorbitol is available either as free flowing granules or as a crystalline powder.

Polyethylene glycols (PEG's) can also be used in the present compositions. These materials are polymers of ethylene oxide with the generalized formula $HOCH_2(CH_2OCH_2)_nCH_2OH$. The use of PEG's alone is not favored but their use in combination with other fillers is acceptable. The molecular weights found most desirable are between 4000 and 6000.

Fillers are generally used in the present invention at a level of from about 85% to about 99.8%, preferably from about 90% to about 98%, most preferably from about 94% to about 97%.

OPTIONAL COMPONENTS

Acceptable lozenges may be manufactured using just the active ingredient, the lubricant and the filler material as outlined above. However, in order to make the lozenges more acceptable from an aesthetic viewpoint, generally included are materials such as spray-dried or encapsulated flavors or liquid flavors adsorbed onto a suitable diluent. Spray dried or encapsulated flavors are preferred. Suitable flavors include oil of peppermint, oil of wintergreen, oil of sassafras, oil of spearmint and oil of clove.

Sweetening agents are also acceptable for use in the present compositions. Suitable agents include aspartame, acesulfame, saccharin, dextrose and levulose. Sweetening and flavoring agents are generally used in the compositions of this invention at levels of from about 0.1% to about 2%, preferably from about 0.25% to about 1.5%.

It is also acceptable to have a solid form of a water-soluble fluoride compound present in the present lozenges in an amount sufficient to give a fluoride concentration of from about 0.0025% to about 0.5% by weight, preferably from about 0.005% to about 2.0% by weight, to provide additionally anticaries effectiveness. Preferred fluorides are sodium fluoride, stannous fluoride, indium fluoride, and sodium monofluorophosphate. Norris et al., U.S. Pat. No. 2,946,735, issued July 26, 1960 and Widder et al., U.S. Pat. No. 3,678,154, issued July 18, 1972 disclose such salts as well as others.

The size and shape of the present lozenges are not critical so long as the lozenge can be easily dissolved in the mouth. Exemplary shapes, weighing from about one to four grams, include cubes, spheres, saucer shapes, cones, cylinders and rectangular parallelopipeds among many others. A convenient shape is a rectangular parallelopiped measuring 1.5 cm × 1.5 cm × 0.5 cm.

METHOD OF MANUFACTURE

A method for manufacturing the lozenges of the present invention is given in Example I

COMPOSITION USE

The lozenges of the present invention are dissolved in the mouth thereby releasing the antimicrobial agent.

The following examples further describe and demonstrate preferred embodiments with the scope of the present invention. The examples are given solely for illustration and are not to be construed as limitations of this invention as many variations thereof are possible without departing from the invention's spirit and scope.

EXAMPLES I-III

The following are chlorhexidine lozenges of the present invention.

| Component | Composition Weight % | | |
| --- | --- | --- | --- |
| | I | II | III |
| Chlorhexidine diacetate | 0.334 | 0.501 | 0.668 |
| Aspartame | 0.250 | 0.250 | 0.250 |

-continued

| Component | Composition Weight % | | |
|---|---|---|---|
| | I | II | III |
| Flavor | 1.500 | 1.500 | 1.500 |
| Sorbitol | 96.916 | 96.749 | 96.582 |
| Lubricant[1] | 1.000 | 1.000 | 1.000 |

[1]Sterotex—Hydrogenated Vegetable Oil N.F. offered by Stokely VanCamp.

These compositions are prepared by mixing the active, sweetener, flavor and filler together in a Patterson-Kelley 16-quart, Model LB-16P, Liquid-Solids Laboratory Twin Shell Blender and mixing for about 45 minutes. The lubricant is then added and an additional 45 minutes of mixing is carried out. The powder is then transferred to a tablet press and the tablets are formed using 70 kN of pressure.

These compositions possess effective antiplaque activity and good consumer properties. In the compositions chlorhexidine may be replaced by other substituted guanidines such as alexidine or quaternary compounds such as cetyl pyridinium chloride, tetradecyl pyridinium chloride, tetradecyl ethyl pyridinium chloride and benzethonium chloride. Likewise sorbitol may be replaced in whole or in part by mannitol or in part by polyethylene glycols or a mixture of mannitol and polyethylene glycols or mixtures of all three.

EXAMPLE IV

The biocidal activity of chlorhexidine in lozenges containing either magnesium stearate or Sterotex lubricant (as described in the preceding examples). The Sterotex product was as set forth in Example I while the magnesium stearate product had the following composition.

| Component | Weight % |
|---|---|
| Sorbitol | 97.416 |
| Magnesium stearate | 0.500 |
| Aspartame | 0.250 |
| Chlorhexidine diacetate | 0.334 |
| Flavor | 1.500 |

A representative lozenge of each type was ground to a fine powder and sufficient powder was weighed into a glass vial to yield a final concentration of 200 ppm chlorhexidine in 10 ml. Nine ml of water was added to the vial after which the vial was shaken well to dissolve the powder. Test bacteria, E. coli, in an amount of one ml of log 7.4/ml concentration was introduced into the vial one minute after the water was added. Survival of the bacteria was then monitored over time with the following results.

| | Log Bacteria Surviving at Indicated Time (Min.) | | | |
|---|---|---|---|---|
| | $\frac{1}{2}$ | 1 | $1\frac{1}{2}$ | 3 |
| Sterotex | 3.0 | <2 | <2 | <2 |
| Magnesium Stearate | 4.5 | 4.6 | 4.2 | 2.3 |

The composition of this invention clearly demonstrates superiority over a composition using a lubricant not within the scope of the claimed invention.

What is claimed is:

1. A non-cariogenic lozenge consisting essentially of from about 0.02% to about 1% of a cationic antimicrobial, from about 0.1% to about 4% of a nonionic lubricant selected from the group consisting of polyethylene glycols, hydrogenated tallow, hydrogenated vegetable oil and mixtures thereof and from about 85% to about 99.8% of a filler selected from the group consisting of mannitol, sorbitol, xylitol, polyethylene glycol, non-cariogenic dextrans and mixtures thereof, wherein said lozenge is substantially free of magnesium stearate.

2. A lozenge according to claim 1 wherein the cationic antimicrobial is selected from the group consisting of quaternary ammonium compounds, substituted guanidines and mixtures thereof.

3. A lozenge according to claim 2 wherein the cationic antimicrobial agent is a substituted guanidine.

4. A lozenge according to claim 2 wherein the cationic antimicrobial agent is a quaternary ammonium compound.

5. A lozenge according to claim 3 wherein the lubricant is hydrogenated vegetable oil.

6. A lozenge according to claim 5 wherein the filler is selected from the group consisting of sorbitol, mannitol and mixtures thereof.

7. A lozenge according to claim 6 wherein the cationic antimicrobial agent is chlorhexidine.

8. A lozenge according to claim 7 which in addition contains a sweetening agent and a flavoring agent.

* * * * *